United States Patent [19]

Chandler

[11] 4,084,005
[45] Apr. 11, 1978

[54] CONTROL OF THE HARMFUL EFFECTS OF FUSARIUM UPON PLANTS

[75] Inventor: Charles M. Chandler, Columbus, Ga.

[73] Assignee: PPG Industries, Inc., Pittsburgh, Pa.

[21] Appl. No.: 735,925

[22] Filed: Oct. 27, 1976

[51] Int. Cl.$^2$ .............................................. A01N 9/14
[52] U.S. Cl. .................................. 424/337; 260/607 A
[58] Field of Search .......................................... 424/337

[56] References Cited

U.S. PATENT DOCUMENTS

| 3,443,012 | 5/1969 | Weil et al. | 424/337 |
| 3,689,567 | 9/1972 | Shen et al. | 424/337 |

Primary Examiner—V. D. Turner
Attorney, Agent, or Firm—Robert J. Grassi

[57] ABSTRACT

Disclosed is a method of controlling the harmful effects of fungus of the genus Fusarium, especially *Fusarium oxysporum f. lycopersici*, upon plants, especially tomato plants by contacting the plant with bis(4-chlorophenyl)-methyl methyl sulfone, prior to infestation by the fungus.

7 Claims, No Drawings

CONTROL OF THE HARMFUL EFFECTS OF FUSARIUM UPON PLANTS

CROSS REFERENCE TO RELATED APPLICATIONS

Copending applications of Assignee are: BIS(4-CHLOROPHENYL) METHYL METHYL SULFOXIDE by George G. Ecke, Ser. No. 701,383, filed June 30, 1976, and NOVEL DI(ARYL) METHYL ALKYL SULFONES by George G. Ecke, Ser. No. 703,168, filed July 7, 1976.

BACKGROUND OF THE INVENTION

1. Field of the Invention

This invention relates to methods of controlling fungus of the genus Fusarium particularly *Fusarium oxysporum f. lycopersici* with bis(aryl)methyl alkyl sulfones, particularly bis(4-chlorophenyl)methyl methyl sulfone.

2. Description of the Prior Art

Because fungi cause harmful effects, such as diseases, which affect crop and ornamental plants, chemical compounds are required to control these harmful effects by preventing or eradicating them. The action of a chemical towards a specific fungus is not a priori predictable, because of very complicated biochemical reactions. For example, a compound may act as a respiratory enzyme which causes respiratory malfunction in the attacking fungus, or as a growth hormone which stimulates a rapid growth causing the fungus to die, or as a metabolite within the plant which stimulates the plant to fight off the disease or to kill the fungus.

Fungi of the genus Fusarium, particularly the species *Fusarium oxysporum f. lycopersici*, harmfully affects plants, such as tomato plants, with a wilt disease called Fusarium Wilt of Tomatoes. These are fungi which need to be controlled. Although certain sulfides, sulfoxides, and sulfones possess biochemical activity against certain organisms, as shown in the following prior art; nothing therein suggests controlling the harmful effects of Fusarium fungi with bis(4-chlorophenyl)methyl methyl sulfone.

For example, bis(4-chlorophenyl)methyl methyl sulfide is active against the mosquito species, *Anopheles albimanus*, as described by R. L. Metcalf *et al*, *Bulletin of the World Health Organization*, Vol. 38, pages 633–647, (1968). Phenylmercaptomethane sulfonamide is described as being active against *Phytophthora infestans* (U.S. Pat. No. 3,412,149). Oximidomethane sulfonamides are disclosed as being active against bacteria and weeds (U.S. Pat. No. 3,549,702). 4-Methoxyphenyl diiodomethyl sulfone is shown to inhibit the growth of Aspergillus oryzae (U.S. Pat. No. 3,615,745), and 2,4,5,4'-tetrachlorodiphenyl sulfide, sulfoxide, and sulfones are shown to be effective against Red Spider Mites (U.S. Pat. No. 3,054,719). Other sulfones, sulfides, and sulfoxides are described but their activity against fungus are not known. For example, certain aryl sulfoxides are described by C. Shunk el al (U.S. Pat. No. 3,466,377), of the type B—X—C(Ar) (Ar')—SO$_2$—R wherein B is a lower aliphatic tertiary-amino group, X is a lower alkylene group, Ar and Ar' are aryl groups, and R is an alkyl group, as analgetics. 4,4'-Chlorodiphenyl sulfone is claimed as an important monomer for preparing polyarylene polyethers (U.S. 3,415,887). Other aryl sulfones are described as both analgetics and anti-pyretics by C. Shunk et al (U.S. Pat. No. 3,637,803 and U.S. Pat. No. 3,689,567); Jean A. Gautier et al in U.S. Pat. No. 3,624,094 describes alpha-[(phenyl sulfinyl) methyl]-alpha phenyl derivatives of pyridinemethanols as analgetics and anti-inflammatory agents.

SUMMARY OF THE INVENTION

The harmful effects of Fusarium fungi, particularly *Fusarium oxysporum f. lycopersici* are controlled by contacting plants, especially by soil drench applications, with bis(4-chlorophenyl)methyl methyl sulfone.

DESCRIPTION OF THE PREFERRED EMBODIMENTS

The harmful effects, that is diseases or irregular growth caused by a fungus of the genus Fusarium upon a plant, is controlled by contacting the plant with bis(4-chlorophenyl)methyl methyl sulfone in an amount which is effective to control the harmful effects of the fungus upon the plant, as illustrated by the following examples.

a. Synthesis of the Sulfone

Bis(4-chlorophenyl)methyl methyl sulfone, which has the structural formula

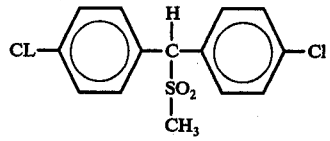

was synthesized as follows:

EXAMPLE I

1. Hydrogenation of 4,4'-Dichlorobenzophenone to 4,4'-Dichlorobenzhydrol

Sodium borohydride (0.164 mole) 6.25 grams in 300 ml. of ethanol was slowly added over a 30 minute period to a refluxing solution of 74.3 grams (0.296 mole) of 4,4'-dichlorobenzophenone (Eastman 1440) in 250 ml. of ethanol, and refluxing was continued for an additional 30 minutes. Then a 100 ml. aqueous solution containing 43.5 grams of acetic acid was added dropwise until hydrogen evolution stopped, whereupon the remainder was rapidly added. A white precipitate formed and was collected by filtration. A 300 ml. aqueous slurry containing this precipitate was warmed to above 95° C., cooled, and filtered, and 74.1 grams (99 percent) of 4,4'-dichlorobenzhydrol, a white solid product having a melting point of 92.5°–94° C., was obtained.

2. Preparation of Chloro-bis(p-chlorophenyl)methane

A solution of 60.02 grams (0.237 mole) of the 4,4'-dichlorobenzhydrol (prepared above) in 175 ml. of toluene, was refluxed and distilled to remove traces of water; then 42 grams (0.356 mole) of thionyl chloride under anhydrous conditions was slowly added during a one hour period. The solution was refluxed and then distilled to remove excess thionyl chloride. The remaining solvent was removed by distillation under vacuum.

The crude product (68.9 grams) was recrystallized twice from 2,2,4-trimethylpentane to give 49.2 grams (76 percent) of chloro-bis(p-chlorophenyl)methane, melting point 61.5°–62.5° C.

3. Preparation of Bis(p-chlorophenyl)methyl methyl sulfide

Chloro-bis(p-chlorophenyl)methane (prepared above) (0.130 mole, 35.2 grams) was added to a cold sodium mercaptide solution formed by distilling 0.205 mole (9.8 grams) of methyl mercaptan into a stirred, cooled solution (0° C.) of ethanolic sodium ethoxide (157 ml., 1.038 N, 0.163 grams). Upon warming, a precipitate of sodium chloride formed, and after refluxing this mixture for two hours and then mixing with water, an oil formed which was extracted with three portions of methylene chloride (30 ml.). The methylene chloride solvent was distilled off under vacuum, leaving 36.7 grams (100 percent) of a white solid with a melting point of 55.5°–57° C. Recrystallization from 2,2,4-trimethylpentane at 0° C. gave a 92 percent yield of the white solid bis(p-chlorophenyl)methyl methyl sulfide (melting point 56°–57° C.).

Analysis Calculated For: $C_{14}H_{12}Cl_2S$: C, 59.37; H, 4.27; and S, 11.32; Found: C, 59.25; H, 4.20; and S, 11.1.

4. Preparation of Bis(p-chlorophenyl)methyl methyl sulfoxide

A solution of 10.7 grams (0.0525 mole) of m-chloroperbenzoic acid in 150 ml. of chloroform was slowly added to a cool solution (5°–7° C.) of 14.1 grams (0.050 mole) of bis(p-chlorophenyl)methyl methyl sulfide (prepared above) in 500 ml. of chloroform, and the resulting solution stirred for two hours at a temperature of 5° C., while a white precipitate formed. The mixture after warming to ambient temperature and holding at this temperature for a two hour period was then mixed with a solution having 20 grams of potassium carbonate in 200 ml. of water. The chloroform phase was then removed and washed with 100 ml. of water, and the chloroform distilled off by vacuum distillation leaving 14.7 grams of a crude product which was recrystallized twice from 2,2,4-trimethylpentane-benzene (2:1) mixture to yield 11.7 grams (78 percent) of the white colored solid of bis(p-chlorophenyl)methyl methyl sulfoxide with a melting point of 109.5°–110.5° C.

Analysis Calculated For: $C_{14}H_{12}Cl_2O_2S$: C, 53.34; H, 3.83; and S, 10.17; Found: C, 56.18; H, 4.04; and S, 10.5.

5. Preparation of Bis(p-chlorophenyl)methyl methyl sulfone

A 250 ml. chloroform solution containing 20.1 grams (0.605 mole) of m-chloroperbenzoic acid was slowly added over a 25 minute period to 250 ml. of a cool (5° C.) chloroform solution containing 14.1 grams (0.050 mole) of bis(p-chlorophenyl)methyl methyl sulfide (prepared above). The temperature of 5° C. was maintained for two hours and then the solution was mixed with an aqueous solution of 40 grams of potassium carbonate in 200 ml. of water, the chloroform phase was removed, washed with water, and the chloroform distilled off by vacuum distillation. The product was recrystallized from a 2,2,4-trimethylpentane-benzene mixture (three times) and then dissolved in methanol. The methanol was distilled off and the crystals which remained were recrystallized a second time from methanol to give 8.7 grams (56 percent yield) of white crystals of bis(p-chlorophenyl)methyl methyl sulfone, melting point 93°–94.5° C.

Analysis Calculated For: $C_{14}H_{12}Cl_2O_2S$: C, 53.34; H, 3.83; and S, 10.17; Found: C, 53.32; H, 3.83; and S, 10.1.

b. Examples of Control By Systemic Soil Drench Application

Bis(4-chlorophenyl)methyl methyl sulfone prepared as above, was emulsified in a solution containing 99.75 percent by volume acetone, 0.05 percent TWEEN 20 ® (sorbitan monooleate polyalkylene derivative) and 0.20 percent SPAN 85 ® (sorbitan trioleate). This solution was diluted with water to the appropriate volume required to apply the sulfone at the rates of 20, 10, and 5 pounds of bis(4-chlorophenyl)methyl methyl sulfone per surface acre per 6 inch depth of soil.

The sulfone solution was applied as a soil drench to the root balls of Bonny Best variety tomato plants which were grown in a greenhouse in sterile soil under natural sunlight at 70° to 80° F. and 50 to 90 percent relative humidity for four to six weeks, at which time the plants were about 6 to 8 inches tall with three to four true leaves.

Forty-eight hours after the soil drench applications, the plants were inoculated by uprooting them and placing the root balls in a solution containing spores of *Fusarium oxysporum f. lycopersici* for a sufficient time to allow the roots to take up the spores.

The inoculated plants were then returned to the sterile soil from which they had been removed and grown as described above in the greenhouse for another four weeks by which time wilt symptoms, if they are present, occur.

The effectiveness of the treatment was determined by directly comparing the disease incidence of treated-inoculated plants with disease incidence of untreated-inoculated controls and is expressed as percent control.

EXAMPLE II

When bis(4-chlorophenyl)methyl methyl sulfone was applied as described herein at 20 pounds per acre per 6 inch depth of soil the percent control was 41 percent, there appeared to be a slight injury to the plant.

EXAMPLE III

When bis(4-chlorophenyl)methyl methyl sulfone was applied as described herein at 10 pounds per acre per 6 inch depth of soil the percent control was 59 percent.

EXAMPLE IV

When bis(4-chlorophenyl)methyl methyl sulfone was applied as described herein at 5 pounds per acre per 6 inch depth of soil the percent control was 62 percent.

In Examples II, III, and IV the untreated plants had a severe wilt from which they did not recover.

c. Controlling the Harmful Effects of the Fungus

1. Formulations

Suitable agricultural compositions containing bis(4-chlorophenyl)methyl methyl sulfone synthesized as illustrated or by other chemical routes are solutions, aerosol sprays, dusts, wettable powders, and emulsifiable concentrates. These types of agricultural compositions may also contain other herbicides, nematocides, pesticides, bactericides, fungicides, or fertilizers or other suitable agricultural substances which are compatible with the sulfone so that the zone or area treated with the composition is rid of many pests, or organisms which interfere with healthy growth of the plants.

In these types of agricultural compositions containing a compound or mixture of the compounds, the sulfone itself may be from 0.1 to 99 weight percent of the composition, which varies with the type of composition, the extent of disease to be controlled, the time of season, and the manner of application.

When a compound, such as bis(p-chlorophenyl)-methyl methyl sulfone is used alone, it may be formulated as a granule of relatively large size, but preferably it is used with other agricultural substances which enhance its application.

A suitable agricultural composition in the form of a solution would be composed of one or more solvents in which bis(4-chlorophenyl) methyl methyl sulfone is completely soluble. Such solution should contain a surfactant such as TWEEN 20 ®, to increase the wettability of the solution. Other solutions would be aerial spray formulations such as pressurized spray solutions, e.g., aerosols, which use one or more low boiling dispersants or solvents such as Freon. The amount of the compound will depend upon the solubility which is effected by the temperature and other ingredients.

Dusts, which also are suitable agricultural compositions, are mixtures of the active compound, e.g., bis(p-chlorophenyl)methyl methyl sulfone, with one or more finely powdered solids having an average particle size of less than 50 microns, such as talc, attapulgite clay, kieselguhr, and other organic and inorganic solids which act as dispersants and carriers for the compound. A typical dust formulation for a suitable agricultural composition will contain from 1.0 to 10.0 parts by weight of bis(p-chlorophenyl)methyl methyl sulfone, and the balance of the composition is divided between the other ingredients.

In applicable situations these dust formulations may be formulated for aerial spraying, by using relatively coarse powders or particles coated with the compounds.

Other suitable agricultural compositions are wettable powders. These are finely divided particles which are dispersible in water or other liquids. The wettable powder is applied to the soil, seed, or plant as a dry dust, or as a water or other liquid emulsion.

Carriers suitable for wettable powder formulations are Fuller's Earth, kaolin clays, silicas, and other highly absorbent, readily wettable inorganic diluents. Wettable powders generally contain about 5 to 80 weight percent of the active ingredient or ingredients, depending upon the carrier absorbency. They usually contain a small amount of a wetting, dispersing, or emulsifying agent to aid dispersion.

Representative surfactants for use as wetting, dispersing, and emulsifying agents in agricultural compositions are alkyl and alkylaryl sulfonates and sulfates and their alkali salts; polyethylene oxides, sulfoxided oils, fatty acid esters of polyhydric alcohols, and other surface active agents, e.g., TWEEN 20®, a commercial surfactant. These surfactants, if used, would vary from 0.25 to 15 weight percent of the composition.

A useful wettable powder formulation for example, comprises about 80.8 parts of bis(p-chlorophenyl)-methyl methyl sulfone, 17.9 parts of Palmetho clay, and as wetting agents, 1.0 part of sodium lignosulfate and 0.3 parts of sulfonated aliphatic polyester. Another useful formulation contains 50 weight percent of the sulfone, about 40 weight percent of hydrated silica, and about 10 weight percent of emulsifiers chosen from those described above. The powder is produced by mixing the desired ingredients and milling them to a suitably fine particle size, such as 1 to 200 microns, but preferably under 74 microns.

All of the wettable powder formulations described may contain one or more compatible agriculturally suitable compounds such as herbicides, fertilizers, pesticides, bactericides, fungicides, or other ingredients which serve to enhance healthy growth of crops.

All of the wettable powder formulations described may be utilized, for example, by mixing the wettable powder formulations with a suitable quantity of water such as 4 to 20 gallons of water per pound of formulation (480 to 8,000 kilogram per cubic meter), and then applied to the crop land by the use of aerial or land-based spraying equipment at practical rate, e.g., 10 to 100 gallons per acre (0.09 to 0.94 cubic meters per hectare). The spraying rate is coordinated with the amount of material to be applied in order to give the desired weight of active ingredient per unit of area.

Other suitable agricultural compositions are emulsifiable concentrates, which are liquid or paste compositions that are dispersible in water or other liquids. These types of compositions containing the sulfone may have a liquid or solid emulsifying agent and may also contain a liquid carrier, such as xylene, heavy aromatic naphthas or other nonvolatile organic solvents. The liquid or solid emulsifying agent, or surfactant may be one of those previously described.

These emulsifiable concentrates are generally dispersed in a liquid carrier, e.g., water, and applied as a spray to the area or plant to be treated. The weight percent of bis(p-chlorophenyl)methyl methyl sulfone in these concentrates varies with the application procedure, but is generally from 0.5 to 95 weight percent.

All of the emulsifiable concentrates may contain one or more other compatible agricultural ingredients which enhance the usefulness of the agricultural composition to stimulate and increase production of healthy plants.

d. Application of the Sulfone to the Plants

As used herein and in the claims, the phrase "contacting the plant with bis(4-chlorophenyl)methyl methyl sulfone" means any manner of causing the sulfone to contact the plant. For example, by spraying a solution of the compound itself or a composition containing bis(4-chlorophenyl)methyl methyl sulfone as active ingredient upon the plant or upon the soil in the vicinity of the roots of the plant. Other ways of contacting the plant are by dusting the plant with granules of the sulfone, or with granules of other agricultural formulations described herein or spraying the plant or the soil in the vicinity of the plant with agricultural formulations described herein.

Preferably the plant is contacted with the compound prior to infestation of the plant with the fungus. This contact can be by a single application of the compound to the plant or by several applications to the plant, such as to the foliage or to the roots of the plant by soil drench applications. Soil drench applications are preferred.

Contacting the plant with bis(4-chlorophenyl)methyl methyl sulfone by applying the sulfone to the soil in the vicinity of the roots of the plants before the plant is infested with the fungus is especially preferred.

As used herein and in the claims, the phrase "applying the sulfone to the soil in the vicinity of the roots of the plants" means any manner of applying the compound itself or as a formulation described herein whereby the bis(4-chlorophenyl)methyl methyl sulfone itself is effectively taken up by the plant and its root system so as to control the harmful effects of the fungus upon the plant. This can be by applying a solution of the sulfone to the soil in the vicinity of the roots of the plant, by applying granules or dusts containing the sulfone as an active ingredient to the soil around the plant roots and then watering or irrigating the soil in such a manner that the sulfone or a metabolite of it is taken up by the plant.

The phrase "to control the harmful effects of the fungus upon the plant" as used herein and in the claims means that from 25 to 100 percent of the plants contacted with the sulfone are free from the harmful effects of the fungus such as disease caused by the fungus when exposed to these fungus, or are only slightly affected by the disease so that they readily recover.

The phrase "in an amount effective to control the harmful effects of the fungus upon the plant" means that amount necessary to achieve control. This amount will vary with the number of fungus present in the growing area, the temperature, the plants and their size, the environment, and the type of application and formulation used. However, this amount generally is from 1000 to 20,000 parts per million (ppm) applied as a solution onto the foliage of the plant to the dripping point. Normally 1000 to 10,000 parts per million are used, but usually 1000 to 5000 parts per million are used. For systemic soil drench applications, that is where the sulfone is applied to the soil so that it is taken up by the roots, the amount is generally from one (1) pound of the sulfone per acre of 6 inch depth of soil to fifty pounds per acre of 6 inch depth of soil. Normally the rate is from two pounds to thirty pounds per acre of 6 inch depth of soil, but usually from three to ten pounds per acre per 6 inch depth of soil is used.

The term "plants" as used herein and in the claim refers to those plants normally affected by the *Fusarium oxysporum*, especially *Fusarium oxysporum f. lycopersici*. Examples of the plants affected by *Fusarium oxysporum* are: tomato, muskmellon, potato, and sweetpotato.

While the invention has been described with reference to specific details for certain illustrative embodiments it is not intended that it shall be limited thereby except insofar as such details appear in the accompanying claims.

I claim:

1. A method of controlling the harmful effects of a fungus of the genus Fusarium upon plants which comprises:
    contacting the plant with bis(4-chlorophenyl)methyl methyl sulfone in an amount effective to control the harmful effects of the fungus upon the plant.

2. The method of claim 1, wherein the step of contacting the plant comprises applying the bis(4-chlorophenyl)methyl methyl sulfone to the foliage of the plant before the plant is infested with the fungus.

3. The method of claim 2, wherein the fungus is *Fusarium oxysporum f. lycopersici*.

4. The method of claim 3, wherein the plant is tomato.

5. The method of claim 1, wherein the step of contacting the plant comprises applying the bis(4-chlorophenyl)methyl methyl sulfone to the soil in the vicinity of the roots of the plant before the plant is infested with the fungus.

6. The method of claim 5, wherein the fungus is *Fusarium oxysporum f. lycopersici*.

7. The method of claim 6, wherein the plant is tomato.

* * * * *